(12) United States Patent
Bissantz et al.

(10) Patent No.: US 9,751,870 B2
(45) Date of Patent: Sep. 5, 2017

(54) OXYTOCIN RECEPTOR AGONISTS FOR THE TREATMENT OF CNS DISEASES

(71) Applicant: Hoffmann-La Roche Inc., Little Falls, NJ (US)

(72) Inventors: Caterina Bissantz, Village-Neuf (FR); Christophe Grundschober, Rodersdorf (CH); Matthias Nettekoven, Grenzach-Wyhlen (DE); Jean-Marc Plancher, Hagenthal-le-Bas (FR); Walter Vifian, Gelterkinden (CH)

(73) Assignee: HOFFMAN-LA ROCHE INC., Little Falls, NJ (US)

( * ) Notice: Subject to any disclaimer, the term of this patent is extended or adjusted under 35 U.S.C. 154(b) by 123 days.

(21) Appl. No.: 14/802,469

(22) Filed: Jul. 17, 2015

(65) Prior Publication Data

US 2015/0322058 A1    Nov. 12, 2015

Related U.S. Application Data

(63) Continuation of application No. PCT/EP2014/050526, filed on Jan. 14, 2014.

(30) Foreign Application Priority Data

Jan. 17, 2013  (EP) .................... 13151632

(51) Int. Cl.
| | |
|---|---|
| *C07D 417/04* | (2006.01) |
| *C07D 401/04* | (2006.01) |
| *C07D 231/42* | (2006.01) |
| *C07D 403/04* | (2006.01) |
| *A61K 31/415* | (2006.01) |
| *A61K 31/427* | (2006.01) |
| *A61K 31/433* | (2006.01) |
| *A61K 31/4439* | (2006.01) |
| *A61K 31/506* | (2006.01) |

(52) U.S. Cl.
CPC .......... *C07D 417/04* (2013.01); *A61K 31/415* (2013.01); *A61K 31/427* (2013.01); *A61K 31/433* (2013.01); *A61K 31/4439* (2013.01); *A61K 31/506* (2013.01); *C07D 231/42* (2013.01); *C07D 401/04* (2013.01); *C07D 403/04* (2013.01)

(58) Field of Classification Search
None
See application file for complete search history.

(56) References Cited

FOREIGN PATENT DOCUMENTS

| | | | |
|---|---|---|---|
| BE | 655242 A | 5/1965 | |
| DE | 1115261 B | 10/1961 | |
| EP | 2221298 A1 | 8/2010 | |
| GB | 865341 A | * 4/1961 | .......... C07D 231/42 |
| GB | 893755 A | * 4/1962 | .......... C07D 231/42 |

OTHER PUBLICATIONS

Rossato et al., "Probing small-molecule binding to cytochrome P450 2D6 and 2C9: An in silico protocol for generating toxicity alerts" CHEMMEDCHEM 5:2088-2101 ( 2010).
Written Opinion for PCT/EP2014/050526.

* cited by examiner

*Primary Examiner* — Jeffrey S Lundgren
*Assistant Examiner* — Michael Schmitt
(74) *Attorney, Agent, or Firm* — Tamara A. Kale

(57) ABSTRACT

The invention relates to the use of a compound of formula I wherein
$A^1$ is phenyl or a five or six membered hereroaryl group, containing 1, 2 or 3 heteroatoms, selected from N or S;
$R^1$ is hydrogen, lower alkyl, halogen, lower alkyl substituted by halogen or cycloalkyl;
$A^2$ is phenyl;
$R^2$ is halogen, lower alkyl, lower alkyl substituted by halogen, lower alkoxy substituted by halogen, cyano, S-lower alkyl substituted by halogen, $S(O)_2$-lower alkyl substituted by halogen;
n is 1 or 2;
or a pharmaceutically acceptable acid addition salt, or a racemic mixture or its corresponding enantiomer and/or optical isomers thereof, for the treatment of autism, stress, including post traumatic stress disorder, anxiety, including anxiety disorders and depression, schizophrenia, psychiatric disorders and memory loss, alcohol withdrawal, drug addiction and for the treatment of Prader-Willi Syndrome.

7 Claims, No Drawings

OXYTOCIN RECEPTOR AGONISTS FOR THE TREATMENT OF CNS DISEASES

This application is a continuation of International Application PCT/EP2014/050526, filed Jan. 14, 2014, which claims the benefit of priority to European Application 13151632.0, filed Jan. 17, 2013, each of which is incorporated herein by reference in its entirety.

The invention relates to the use of a compound of formula I

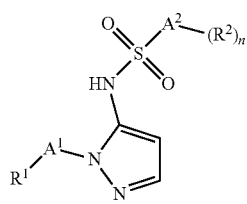

wherein
$A^1$ is phenyl or a five or six membered hereroaryl group, containing 1, 2 or 3 heteroatoms, selected from N or S;
$R^1$ is hydrogen, lower alkyl, halogen, lower alkyl substituted by halogen or cycloalkyl;
$A^2$ is phenyl;
$R^2$ is halogen, lower alkyl, lower alkyl substituted by halogen, lower alkoxy substituted by halogen, cyano, S-lower alkyl substituted by halogen, $S(O)_2$-lower alkyl substituted by halogen;
n is 1 or 2;
or to pharmaceutically acceptable acid addition salt, to a racemic mixture or to its corresponding enantiomer and/or optical isomers thereof for the treatment of autism, stress, including post traumatic stress disorder, anxiety, including anxiety disorders and depression, schizophrenia, psychiatric disorders and memory loss, alcohol withdrawal, drug addiction and for the treatment of Prader-Willi Syndrome.

Substituted benzene-sulfonamide containing a pyrazole group are described in the literature, for example in WO2010118063, BE655242, U.S. Pat. No. 3,014,038, GB893755, DE1115739, DE1115261 and GB865341, as choleretics and for use in the treatment of cancer and hypoglycemia, for use to improve acute and chronic liver disturbances and for activation of the liver-function in the case of hepatic complaints.

It has been found that the present compounds are oxytocin receptor agonists, which compounds are oxytocin analogs that retain oxytocin bioactivity. Such analog molecules are capable of acting in a manner similar to endogenous oxytocin, including binding the oxytocin receptor. Analogs of oxytocin have completely new molecular structures.

Oxytocin is a nine amino acid cyclic peptide hormone with two cysteine residues that form a disulfide bridge between position 1 and 6. Human oxytocin comprises the sequence Cys-Tyr-Ile-Gln-Asn-Cys-Pro-Leu-Gly.

Oxytocin is a potent uterotonic agent for the control of uterine atony and excessive bleeding, clinically used to induce labour, and has been shown to enhance the onset and maintenance of lactation (Gimpl et al., Physiol. Rev., 81, (2001), 629-683, Ruis et al., BMJ, 283, (1981), 340-342). Carbetocin (1-deamino-1-carba-2-tyrosine (O-methyl)-oxytocin) is also a potent uterotonic agent clinically used for the control of uterine atony and excessive bleeding.

Oxytocin agonists may be used for the treatment of Prader-Willi Syndrome, which is a rare genetic disorder which affects one child in 25,000.

Further research indicates that oxytocin agonists are useful for the treatment of inflammation and pain, including abdominal and back pain (Yang, Spine, 19, 1994, 867-71), sexual dysfunction in both male (Lidberg et al., Pharmakopsychiat., 10, 1977, 21-25) and female (Anderson-Hunt, et al., BMJ, 309, 1994, 929), irritable bowel syndrome (IBS, Louvel et al., Gut, 39, 1996, 741-47), constipation and gastrointestinal obstruction (Ohlsson et al., Neurogastroenterol. Motil., 17, 2005, 697-704), autism (Hollander et al., Neuropsychopharm., 28, 2008, 193-98), stress, including post traumatic stress disorder (PTSD) (Pitman et al., Psychiatry Research, 48, 107-117), anxiety, including anxiety disorders and depression (Kirsch et al., J. Neurosci., 25, 49, 11489-93, Waldherr et al., PNAS, 104, 2007, 16681-84), surgical blood loss or control of post-partum haemorrhage (Fujimoto et al., Acta Obstet. Gynecol., 85, 2006, 1310-14), labor induction and maintenance (Flamm et al., Obstet. Gynecol., 70, 1987, 70-12), wound healing and infection, mastitis and placenta delivery, and osteoporosis. Additionally, oxytocin agonists may be useful for the diagnosis of both cancer and placental insufficiency.

Furthermore, the Articles "Intranasal Oxytocin blocks alcohol in human subjects" (Alcohol Clin Exp Res, Vol, No. 2012) and "Breaking the loop: Oxytocin as a potential treatment for drug addiction" (Hormones and Behavior, 61, 2012, 331-339) propose to treat alcohol withdrawal and drug addiction with a oxytocin agonist.

Oxytocin and its receptors exists in areas of the brain implicated in the symptoms of schizophrenia, such as the nucleus accumbens and the hippocampus. The oxytocin receptor agonists may be used for the treatment of autism, stress, including post traumatic stress disorder, anxiety, including anxiety disorders and depression, schizophrenia, Alzheimer's disease, psychiatric disorders, memory loss and metabolic diseases (WO2012/016229).

The compounds of formula I were also functionally tested on cell lines expressing the human Vasopressin 1a and the human Vasopressin 2 receptor to measure potential agonist activity and were found to be selective over the human Oxytocin receptor.

Objects of the present invention are the use of compounds of formula I and novel specific compounds falling into the scope of formula I and their pharmaceutically acceptable salts for the treatment of CNS diseases related to the oxytocin receptor, which diseases are autism, stress, including post traumatic stress disorder, anxiety, including anxiety disorders and depression, schizophrenia, psychiatric disorders and memory loss, alcohol withdrawal, drug addiction and for the treatment of Prader-Willi Syndrome.

Further objects are the preparation of novel compounds of formula I and medicaments, containing them for the treatment of the above-mentioned diseases.

The present invention may provide selective, efficacious compounds, providing alternatives and/or improvements in the treatment of certain CNS diseases including autism, stress, including post traumatic stress disorder, anxiety, including anxiety disorders and depression, schizophrenia, psychiatric disorders and memory loss, alcohol withdrawal, drug addiction and for the treatment of Prader-Willi Syndrome.

As used herein, the term "lower alkyl" denotes a saturated straight- or branched chain group containing from 1 to 7 carbon atoms, for example, methyl, ethyl, propyl, isopropyl, n-butyl, i-butyl, 2-butyl, t-butyl and the like.

As used herein, the term "five or six membered heteroaryl group, containing 1, 2 or 3 heteroatoms selected from N or S" denotes an aromatic ring selected from pyridine, thiazole, pyrimidine or 1,2,4-thiadiazole.

The term "halogen" encompasses chlorine, fluorine, iodine and bromide.

The term "lower alkyl substituted by halogen" denotes a lower alkyl group as defined above, wherein at least one hydrogen atom is replaced by a halogen atom, for example $CF_3$, $CHF_2$ or $CHFCH_3$.

The term "lower alkoxy substituted by halogen" denotes the group O-"lower alkyl substituted by halogen" wherein "lower alkyl substituted by halogen" is as defined above.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

One embodiment of the invention is the use of compounds of formula I for the treatment of autism, stress, including post traumatic stress disorder, anxiety, including anxiety disorders and depression, schizophrenia, psychiatric disorders and memory loss, alcohol withdrawal, drug addiction and for the treatment of Prader-Willi Syndrome.

One further embodiment of the invention is the use of compounds of formula I for the preparation of a medicament for the treatment of treatment of autism, stress, including post traumatic stress disorder, anxiety, including anxiety disorders and depression, schizophrenia, psychiatric disorders and memory loss, alcohol withdrawal, drug addiction and for the treatment of Prader-Willi Syndrome.

A further embodiment of the invention is a method for the treatment of autism, stress, Including Post traumatic stress disorder, anxiety, including anxiety disorders and depression, schizophrenia, psychiatric disorders and memory loss, alcohol withdrawal, drug addiction and for the treatment of Prader-Willi Syndrome, which method comprises administering an effective amount of a compound of formula I.

One further embodiment of the invention is a pharmaceutical composition comprising a novel compound of formula I, selected from the group consisting of 4-Chloro-N-(2-pyridin-2-yl-2H-pyrazol-3-yl)-benzenesulfonamide
N-(2-Pyridin-2-yl-2H-pyrazol-3-yl)-4-trifluoromethyl-benzenesulfonamide
4-Ethyl-N-(2-pyridin-2-yl-2H-pyrazol-3-yl)-benzenesulfonamide
4-Propyl-N-(2-pyridin-2-yl-2H-pyrazol-3-yl)-benzenesulfonamide
2-Chloro-N-(2-pyridin-2-yl-2H-pyrazol-3-yl)-4-trifluoromethyl-benzenesulfonamide
4-Difluoromethoxy-N-(2-pyridin-2-yl-2H-pyrazol-3-yl)-benzenesulfonamide
4-Chloro-N-[2-(4-fluoro-phenyl)-2H-pyrazol-3-yl]-benzenesulfonamide
4-Cyano-N-(2-pyridin-2-yl-2H-pyrazol-3-yl)-benzenesulfonamide
N-[2-(4-Methyl-thiazol-2-yl)-2H-pyrazol-3-yl]-4-trifluoromethyl-benzenesulfonamide
4-Chloro-N-[2-(4-methyl-thiazol-2-yl)-2H-pyrazol-3-yl]-benzenesulfonamide
4-Ethyl-N-[2-(4-methyl-thiazol-2-yl)-2H-pyrazol-3-yl]-benzenesulfonamide
N-(2-Pyrimidin-2-yl-2H-pyrazol-3-yl)-4-trifluoromethyl-benzenesulfonamide
2,4-Dichloro-N-(2-pyridin-2-yl-2H-pyrazol-3-yl)-benzenesulfonamide
4-Chloro-2-fluoro-N-(2-pyridin-2-yl-2H-pyrazol-3-yl)-benzenesulfonamide
4-(1-Fluoro-ethyl)-N-(2-pyridin-2-yl-2H-pyrazol-3-yl)-benzenesulfonamide
N-[2-(4-Methyl-pyridin-2-yl)-2H-pyrazol-3-yl]-4-trifluoromethyl-benzenesulfonamide
4-Chloro-N-[2-(4-methyl-pyridin-2-yl)-2H-pyrazol-3-yl]-benzenesulfonamide
4-Ethyl-N-[2-(4-methyl-pyridin-2-yl)-2H-pyrazol-3-yl]-benzenesulfonamide
4-Cyano-N-[2-(4-methyl-pyridin-2-yl)-2H-pyrazol-3-yl]-benzenesulfonamide
N-(2-Pyridin-2-yl-2H-pyrazol-3-yl)-4-trifluoromethylsulfanyl-benzenesulfonamide
4-Trifluoromethyl-N-[2-(2-trifluoromethyl-pyrimidin-4-yl)-2H-pyrazol-3-yl]-benzenesulfonamide
2-Fluoro-N-(2-pyridin-2-yl-2H-pyrazol-3-yl)-4-trifluoromethyl-benzenesulfonamide
N-(2-Pyridin-2-yl-2H-pyrazol-3-yl)-4-trifluoromethanesulfonyl-benzenesulfonamide
3-Fluoro-N-(2-pyridin-2-yl-2H-pyrazol-3-yl)-4-trifluoromethyl-benzenesulfonamide
N-[2-(3-Cyclopropyl-[1,2,4]thiadiazol-5-yl)-2H-pyrazol-3-yl]-4-ethyl-benzenesulfonamide and
4-Chloro-2-fluoro-N-[2-(4-methyl-thiazol-2-yl)-2H-pyrazol-3-yl]-benzenesulfonamide, and a therapeutically inert carrier.

One embodiment of the invention are novel compounds of formula I, which compounds are 4-Chloro-N-(2-pyridin-2-yl-2H-pyrazol-3-yl)-benzenesulfonamide
N-(2-Pyridin-2-yl-2H-pyrazol-3-yl)-4-trifluoromethyl-benzenesulfonamide
4-Ethyl-N-(2-pyridin-2-yl-2H-pyrazol-3-yl)-benzenesulfonamide
4-Propyl-N-(2-pyridin-2-yl-2H-pyrazol-3-yl)-benzenesulfonamide
2-Chloro-N-(2-pyridin-2-yl-2H-pyrazol-3-yl)-4-trifluoromethyl-benzenesulfonamide
4-Difluoromethoxy-N-(2-pyridin-2-yl-2H-pyrazol-3-yl)-benzenesulfonamide
4-Chloro-N-[2-(4-fluoro-phenyl)-2H-pyrazol-3-yl]-benzenesulfonamide
4-Cyano-N-(2-pyridin-2-yl-2H-pyrazol-3-yl)-benzenesulfonamide
N-[2-(4-Methyl-thiazol-2-yl)-2H-pyrazol-3-yl]-4-trifluoromethyl-benzenesulfonamide
4-Chloro-N-[2-(4-methyl-thiazol-2-yl)-2H-pyrazol-3-yl]-benzenesulfonamide
4-Ethyl-N-[2-(4-methyl-thiazol-2-yl)-2H-pyrazol-3-yl]-benzenesulfonamide
N-(2-Pyrimidin-2-yl-2H-pyrazol-3-yl)-4-trifluoromethyl-benzenesulfonamide
2,4-Dichloro-N-(2-pyridin-2-yl-2H-pyrazol-3-yl)-benzenesulfonamide
4-Chloro-2-fluoro-N-(2-pyridin-2-yl-2H-pyrazol-3-yl)-benzenesulfonamide
4-(1-Fluoro-ethyl)-N-(2-pyridin-2-yl-2H-pyrazol-3-yl)-benzenesulfonamide
N-[2-(4-Methyl-pyridin-2-yl)-2H-pyrazol-3-yl]-4-trifluoromethyl-benzenesulfonamide
4-Chloro-N-[2-(4-methyl-pyridin-2-yl)-2H-pyrazol-3-yl]-benzenesulfonamide
4-Ethyl-N-[2-(4-methyl-pyridin-2-yl)-2H-pyrazol-3-yl]-benzenesulfonamide 4-Cyano-N-[2-(4-methyl-pyridin-2-yl)-2H-pyrazol-3-yl]-benzenesulfonamide N-(2-Pyridin-2-yl-2H-pyrazol-3-yl)-4-trifluoromethylsulfanyl-benzenesulfonamide 4-Trifluoromethyl-N-[2-(2-trifluoromethyl-pyrimidin-4-yl)-2H-pyrazol-3-yl]-benzenesulfonamide 2-Fluoro-N-(2-pyridin-2-yl-2H-pyrazol-3-yl)-4-trifluoromethyl-benzenesulfonamide N-(2-Pyridin-2-yl-2H-pyrazol-3-yl)-4-trifluoromethanesulfonyl-benzenesulfonamide 3-Fluoro-N-(2-pyridin-2-yl-2H-pyrazol-3-yl)-4-trifluoromethyl-benzenesulfonamide N-[2-(3-Cyclopropyl-[1,2,4]thiadiazol-5-yl)-2H-pyrazol-3-yl]-4-ethyl-benzenesulfonamide and 4-Chloro-2-fluoro-N-[2-(4-methyl-thiazol-2-yl)-2H-pyrazol-3-yl]-benzenesulfonamide.

One further embodiment of the invention are compounds of formula IA,

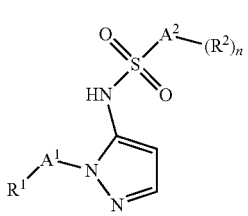

IA wherein

A$^1$ is thiazolyl, pyrimidinyl or 1,2,4-thiadiazolyl;

R$^1$ is hydrogen, lower alkyl, halogen, lower alkyl substituted by halogen or cycloalkyl;

A$^2$ is phenyl;

R$^2$ is halogen, lower alkyl, lower alkyl substituted by halogen, lower alkoxy substituted by halogen, cyano, S-lower alkyl substituted by halogen, S(O)$_2$-lower alkyl substituted by halogen;

n is 1 or 2;

or pharmaceutically acceptable acid addition salt, a racemic mixture or its corresponding enantiomer and/or optical isomers thereof, for example the following compounds N-[2-(4-Methyl-thiazol-2-yl)-2H-pyrazol-3-yl]-4-trifluoromethyl-benzenesulfonamide 4-Chloro-N-[2-(4-methyl-thiazol-2-yl)-2H-pyrazol-3-yl]-benzenesulfonamide 4-Ethyl-N-[2-(4-methyl-thiazol-2-yl)-2H-pyrazol-3-yl]-benzenesulfonamide N-(2-Pyrimidin-2-yl-2H-pyrazol-3-yl)-4-trifluoromethyl-benzenesulfonamide 4-Trifluoromethyl-N-[2-(2-trifluoromethyl-pyrimidin-4-yl)-2H-pyrazol-3-yl]-benzenesulfonamide N-[2-(3-Cyclopropyl-[1,2,4]thiadiazol-5-yl)-2H-pyrazol-3-yl]-4-ethyl-benzenesulfonamide or 4-Chloro-2-fluoro-N-[2-(4-methyl-thiazol-2-yl)-2H-pyrazol-3-yl]-benzenesulfonamide.

The preparation of compounds of formula I of the present invention may be carried out in sequential or convergent synthetic routes. Syntheses of the compounds of the invention are shown in the following scheme. The skills required for carrying out the reactions and purifications of the resulting products are known to those skilled in the art. The substituents and indices used in the following description of the processes have the significance given herein before unless indicated to the contrary. In more detail, the compounds of formula I can be manufactured by the methods given below, by the methods given in the examples or by analogous methods. Appropriate reaction conditions for the individual reaction steps are known to a person skilled in the art. Also, for reaction conditions described in literature affecting the described reactions see for example: Comprehensive Organic Transformations: A Guide to Functional Group Preparations, 2nd Edition, Richard C. Larock. John Wiley & Sons, New York, N.Y. 1999). We find it convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 h to several days will usually suffice to yield the described intermediates and compounds. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by methods known in the art, for example, by processes described below, which process comprises a) reacting a compound of formula

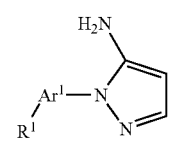

II with a compound of formula

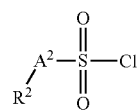

III to a compound of formula

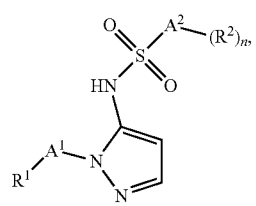

I and, if desired, converting the compounds obtained into pharmaceutically acceptable acid addition salts.

Scheme 1

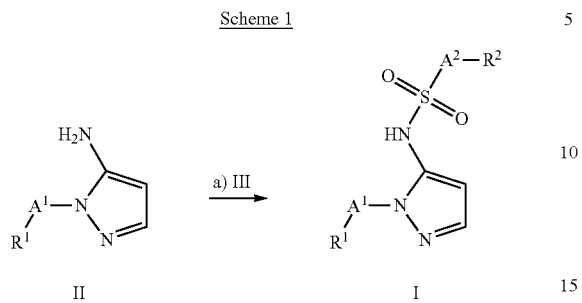

a) Amino-pyrazoles II are either commercially available or can be synthesized in various ways where the procedures are known to those skilled in the art. However, we find it convenient to react II with sulfonylchlorides III (either commercially available or they can be synthesized in various ways where the procedures are known to those skilled in the art) under basic conditions to yield final pyrazole derivatives I.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I may be basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

Compounds of formula I may also be acidic.

EXPERIMENTAL PART

Example 1

4-Chloro-N-(2-pyridin-2-yl-2H-pyrazol-3-yl)-benzenesulfonamide

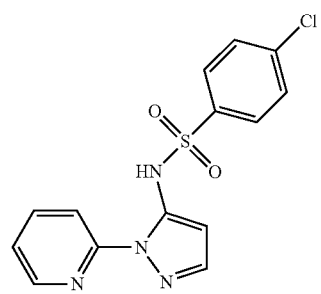 [SMILES: O=S(=O)(Nc1ccnn1-c1ccccn1)c1ccc(Cl)cc1]

A mixture of 16.2 mg (0.1 mmol) 2-pyridin-2-yl-2H-pyrazol-3-ylamine (commercially available) and 26.4 mg (0.125 mmol) 4-chlorobenzene-1-sulfonyl chloride in 1 mL pyridine was reacted at room temperature overnight and evaporated. The residue was taken up in methanol and formic acid and subjected to purification by preparative HPLC on reversed phase eluting with a gradient formed from acetonitrile, water and formic acid. The product containing fractions were evaporated to yield 20.7 mg (58%) of the title compound as viscous yellow oil. MS(m/e): 335.3 (MH$^+$).

Example 2

N-(2-Pyridin-2-yl-2H-pyrazol-3-yl)-4-trifluoromethyl-benzenesulfonamide

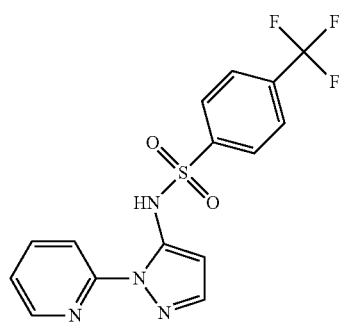 [SMILES: O=S(=O)(Nc1ccnn1-c1ccccn1)c1ccc(C(F)(F)F)cc1]

In analogy to the procedure described for the synthesis of 4-chloro-N-(2-pyridin-2-yl-2H-pyrazol-3-yl)-benzenesulfonamide (example 1) the title compound was prepared from 2-pyridin-2-yl-2H-pyrazol-3-ylamine (commercially available) and 4-(trifluoromethyl)benzene-1-sulfonyl chloride (commercially available) and isolated as off-white solid. MS(m/e): 369.1 (MH$^+$).

Example 3

4-Ethyl-N-(2-pyridin-2-yl-2H-pyrazol-3-yl)-benzenesulfonamide

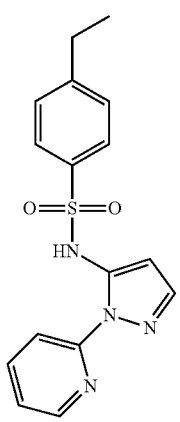 [SMILES: CCc1ccc(S(=O)(=O)Nc2ccnn2-c2ccccn2)cc1]

In analogy to the procedure described for the synthesis of 4-chloro-N-(2-pyridin-2-yl-2H-pyrazol-3-yl)-benzenesulfonamide (example 1) the title compound was prepared from 2-pyridin-2-yl-2H-pyrazol-3-ylamine (commercially available) and 4-ethylbenzene-1-sulfonyl chloride (commercially available) and isolated as yellow viscous oil. MS(m/e): 329.4 (MH$^+$).

Example 4

4-Propyl-N-(2-pyridin-2-yl-2H-pyrazol-3-yl)-benzenesulfonamide

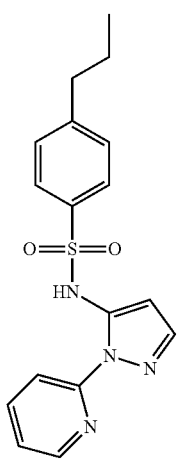 [SMILES: CCCc1ccc(S(=O)(=O)Nc2ccnn2-c2ccccn2)cc1]

In analogy to the procedure described for the synthesis of 4-chloro-N-(2-pyridin-2-yl-2H-pyrazol-3-yl)-benzenesulfonamide (example 1) the title compound was prepared from 2-pyridin-2-yl-2H-pyrazol-3-ylamine (commercially available) and 4-propylbenzene-1-sulfonyl chloride (commercially available) and isolated as yellow viscous oil. MS(m/e): 343.4 (MH$^+$).

Example 5

2-Chloro-N-(2-pyridin-2-yl-2H-pyrazol-3-yl)-4-trifluoromethyl-benzenesulfonamide

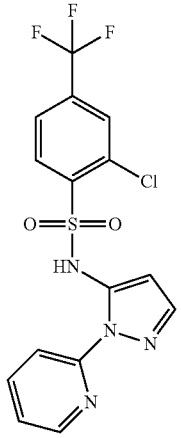 [SMILES: O=S(=O)(Nc1ccnn1-c1ccccn1)c1ccc(C(F)(F)F)cc1Cl]

In analogy to the procedure described for the synthesis of 4-chloro-N-(2-pyridin-2-yl-2H-pyrazol-3-yl)-benzenesulfonamide (example 1) the title compound was prepared from 2-pyridin-2-yl-2H-pyrazol-3-ylamine (commercially available) and 2-chloro-4-(trifluoromethyl)benzene-1-sulfonyl chloride (commercially available) and isolated as light yellow solid. MS(m/e): 403.4 (MH$^+$).

Example 6

4-Difluoromethoxy-N-(2-pyridin-2-yl-2H-pyrazol-3-yl)-benzenesulfonamide

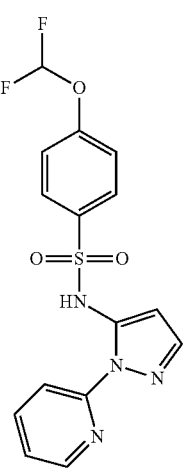 [SMILES: O=S(=O)(Nc1ccnn1-c1ccccn1)c1ccc(OC(F)F)cc1]

In analogy to the procedure described for the synthesis of 4-chloro-N-(2-pyridin-2-yl-2H-pyrazol-3-yl)-benzenesulfonamide (example 1) the title compound was prepared from 2-pyridin-2-yl-2H-pyrazol-3-ylamine (commercially available) and 4-(difluoromethoxy)benzene-1-sulfonyl chloride (commercially available) and isolated as yellow viscous oil. MS(m/e): 367.4 (MH$^+$).

Example 7

4-Chloro-N-[2-(4-fluoro-phenyl)-2H-pyrazol-3-yl]-benzenesulfonamide

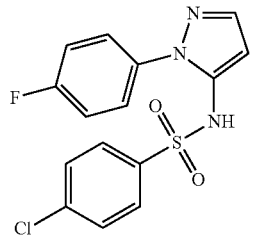 [SMILES: O=S(=O)(Nc1ccnn1-c1ccc(F)cc1)c1ccc(Cl)cc1]

In analogy to the procedure described for the synthesis of 4-chloro-N-(2-pyridin-2-yl-2H-pyrazol-3-yl)-benzenesulfonamide (example 1) the title compound was prepared from 1-(4-fluorophenyl)-1H-pyrazol-5-amine (commercially available) and 4-chlorobenzene-1-sulfonyl chloride (commercially available). MS(m/e): 352.4 (MH+).

Example 8

4-Cyano-N-(2-pyridin-2-yl-2H-pyrazol-3-yl)-benzenesulfonamide

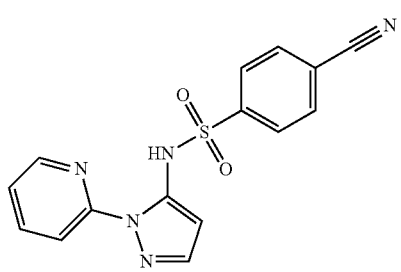 [SMILES: N#Cc1ccc(S(=O)(=O)Nc2ccnn2-c2ccccn2)cc1]

In analogy to the procedure described for the synthesis of 4-chloro-N-(2-pyridin-2-yl-2H-pyrazol-3-yl)-benzenesulfonamide (example 1) the title compound was prepared from 2-pyridin-2-yl-2H-pyrazol-3-ylamine (commercially available) and 4-cyanobenzene-1-sulfonyl chloride (commercially available) and isolated as off-white solid. MS(m/e): 326.4 (MH+).

Example 9

N-[2-(4-Methyl-thiazol-2-yl)-2H-pyrazol-3-yl]-4-trifluoromethyl-benzenesulfonamide

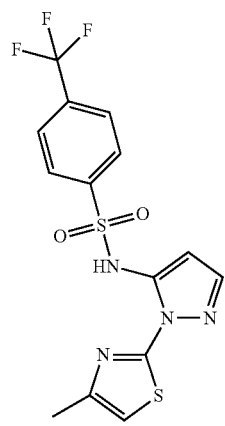 [SMILES: Cc1csc(-n2nccc2NS(=O)(=O)c2ccc(C(F)(F)F)cc2)n1]

a) 2-(4-Methyl-thiazol-2-yl)-2H-pyrazol-3-ylamine

A mixture of 2-hydrazinyl-4-methylthiazole hydrochloride (5 g, 30.2 mmol) and DIPEA (7.8 g, 10.5 mL, 60.4 mmol) in N,N-dimethylacetamide (150 mL) was treated with of 3-(dimethylamino)acrylonitrile (2.9 g, 3.05 mL, 30.2 mmol) and heated to 145° C. for 4 h. The solution was cooled to room temperature and concentrated in high vacuo. The residue was dissolved in DCM (50 mL), absorbed on Isolute HM-N (30 g) and concentrated in vacuo. The residue was purified by silica gel chromatography eluting with a gradient formed from heptane and ethyl acetate to yield after evaporation of the product containing fractions 530 mg (9.5%) of the title compound as light brown solid. MS(m/e): 181.2 (MH+).

b) N-[2-(4-Methyl-thiazol-2-yl)-2H-pyrazol-3-yl]-4-trifluoromethyl-benzenesulfonamide In analogy to the procedure described for the synthesis of 4-chloro-N-(2-pyridin-2-yl-2H-pyrazol-3-yl)-benzenesulfonamide (example 1) the title compound was prepared from 2-(4-methyl-thiazol-2-yl)-2H-pyrazol-3-ylamine and 4-(trifluoromethyl)benzene-1-sulfonyl chloride (commercially available) and isolated as light yellow solid. MS(m/e): 389.5 (MH+).

Example 10

4-Chloro-N-[2-(4-methyl-thiazol-2-yl)-2H-pyrazol-3-yl]-benzenesulfonamide

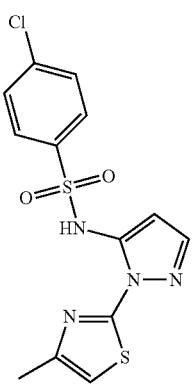 [SMILES: Cc1csc(-n2nccc2NS(=O)(=O)c2ccc(Cl)cc2)n1]

In analogy to the procedure described for the synthesis of 4-chloro-N-(2-pyridin-2-yl-2H-pyrazol-3-yl)-benzenesulfonamide (example 1) the title compound was prepared from 2-(4-methyl-thiazol-2-yl)-2H-pyrazol-3-ylamine and 4-chlorobenzene-1-sulfonyl chloride (commercially available) and isolated as orange solid. MS(m/e): 355.4 (MH+).

Example 11

4-Ethyl-N-[2-(4-methyl-thiazol-2-yl)-2H-pyrazol-3-yl]-benzenesulfonamide

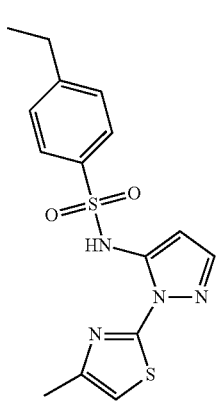 [SMILES: CCc1ccc(S(=O)(=O)Nc2ccnn2-c2nc(C)cs2)cc1]

In analogy to the procedure described for the synthesis of 4-chloro-N-(2-pyridin-2-yl-2H-pyrazol-3-yl)-benzenesulfonamide (example 1) the title compound was prepared from 2-(4-methyl-thiazol-2-yl)-2H-pyrazol-3-ylamine and 4-ethylbenzene-1-sulfonyl chloride (commercially available) and isolated as orange solid. MS(m/e): 349.5 (MH$^+$).

Example 12

N-(2-Pyrimidin-2-yl-2H-pyrazol-3-yl)-4-trifluoromethyl-benzenesulfonamide

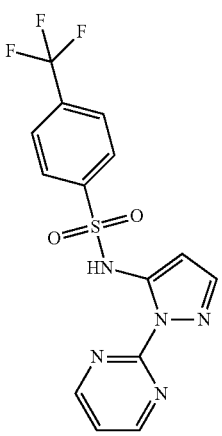 [SMILES: O=S(=O)(Nc1ccnn1-c1ncccn1)c1ccc(C(F)(F)F)cc1]

In analogy to the procedure described for the synthesis of 4-chloro-N-(2-pyridin-2-yl-2H-pyrazol-3-yl)-benzenesulfonamide (example 1) the title compound was prepared from 1-(pyrimidin-2-yl)-1H-pyrazol-5-amine (commercially available) and 4-(trifluoromethyl)benzene-1-sulfonyl chloride (commercially available). MS(m/e): 370.5 (MH$^+$).

Example 13

2,4-Dichloro-N-(2-pyridin-2-yl-2H-pyrazol-3-yl)-benzenesulfonamide

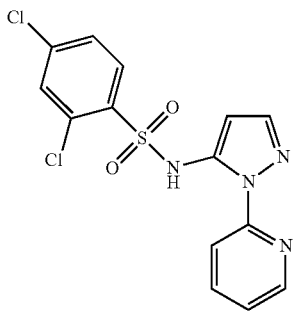 [SMILES: O=S(=O)(Nc1ccnn1-c1ccccn1)c1ccc(Cl)cc1Cl]

In analogy to the procedure described for the synthesis of 4-chloro-N-(2-pyridin-2-yl-2H-pyrazol-3-yl)-benzenesulfonamide (example 1) the title compound was prepared from 2-pyridin-2-yl-2H-pyrazol-3-ylamine (commercially available) and 2,4-dichlorobenzene-1-sulfonyl chloride (commercially available). MS(m/e): 367.4 (MH$^+$).

Example 14

4-Chloro-2-fluoro-N-(2-pyridin-2-yl-2H-pyrazol-3-yl)-benzenesulfonamide

In analogy to the procedure described for the synthesis of 4-chloro-N-(2-pyridin-2-yl-2H-pyrazol-3-yl)-benzenesulfonamide (example 1) the title compound was prepared from 2-pyridin-2-yl-2H-pyrazol-3-ylamine (commercially available) and 4-chloro-2-fluorobenzene-1-sulfonyl chloride (commercially available). MS(m/e): 351.4 (MH$^+$).

Example 15

4-(1-Fluoro-ethyl)-N-(2-pyridin-2-yl-2H-pyrazol-3-yl)-benzenesulfonamide

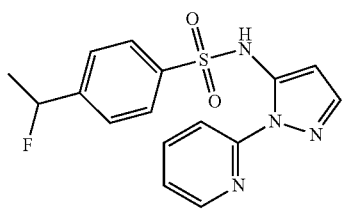 [SMILES: CC(F)c1ccc(S(=O)(=O)Nc2ccnn2-c2ccccn2)cc1]

a) 4-Acetyl-N-(2-pyridin-2-yl-2H-pyrazol-3-yl)-benzenesulfonamide

In analogy to the procedure described for the synthesis of 4-chloro-N-(2-pyridin-2-yl-2H-pyrazol-3-yl)-benzenesulfonamide (example 1) the title compound was prepared from 2-pyridin-2-yl-2H-pyrazol-3-ylamine (commercially available) and 4-acetylbenzene-1-sulfonyl chloride (commercially available) and isolated as light brown solid. MS(m/e): 343.5 (MH$^+$).

b) 4-(1-Hydroxy-ethyl)-N-(2-pyridin-2-yl-2H-pyrazol-3-yl)-benzenesulfonamide A mixture of 4-acetyl-N-(1-(pyridin-2-yl)-1H-pyrazol-5-yl)benzenesulfonamide (200 mg, 0.584 mmol) and NaBH$_4$ (22.1 mg, 0.584 mmol) in THF (20 mL)/MeOH (5 mL) was stirred overnight at room temperature. Na$_2$CO$_3$-solution (10%, aq.) was added and stirred for 30 min. The pH was adjusted to pH 6-7 and the mixture was extracted with ethyl acetate (2×30 mL). The organic layers were washed with brine (1×50 mL), dried over Na$_2$SO$_4$, filtered off and concentrated in vacuo to yield the title compound (193 mg, 0.56 mmol, 96%) as off-white waxy-solid. MS(m/e): 345.5 (MH$^+$).

c) 4-(1-Fluoro-ethyl)-N-(2-pyridin-2-yl-2H-pyrazol-3-yl)-benzenesulfonamide

A mixture of 4-(1-hydroxyethyl)-N-(1-(pyridin-2-yl)-1H-pyrazol-5-yl)benzenesulfonamide (100 mg, 0.290 mmol) and DAST (51.5 mg, 42.2 µl, 0.319 mmol) in DCM (11 mL) at 0-5° C. was stirred for 1 h. NaHCO$_3$-solution (5%, aq., 5 mL) was added and the pH adjusted to pH 6-7. The organic layer was separated and the aqueous layer was extracted with DCM (2×5 mL). The combined organic layers were dried over Na$_2$SO$_4$, filtered off and concentrated in vacuo. The residue was dissolved in methanol (4 mL) and subjected to purification by preparative HPLC on reversed phase to yield after evaporation of the product containing fractions 57 mg (55%) of the title compound as colorless viscous oil. MS(m/e): 347.6 (MH$^+$).

Example 16

N-[2-(4-Methyl-pyridin-2-yl)-2H-pyrazol-3-yl]-4-trifluoromethyl-benzenesulfonamide

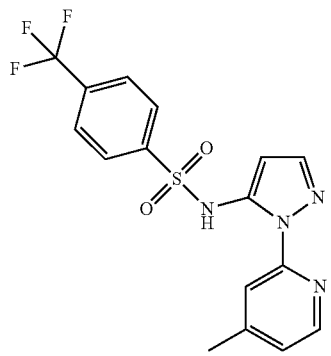 [SMILES: Cc1ccnc(-n2nccc2NS(=O)(=O)c2ccc(C(F)(F)F)cc2)c1]

In analogy to the procedure described for the synthesis of 4-chloro-N-(2-pyridin-2-yl-2H-pyrazol-3-yl)-benzenesulfonamide (example 1) the title compound was prepared from 1-(4-methylpyridin-2-yl)-1H-pyrazol-5-amine (commercially available) and 4-(trifluoromethyl)benzene-1-sulfonyl chloride (commercially available). MS(m/e): 383.5 (MH$^+$).

Example 17

4-Chloro-N-[2-(4-methyl-pyridin-2-yl)-2H-pyrazol-3-yl]-benzenesulfonamide

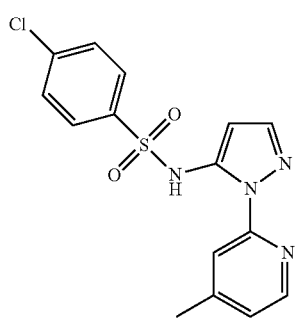 [SMILES: Cc1ccnc(-n2nccc2NS(=O)(=O)c2ccc(Cl)cc2)c1]

In analogy to the procedure described for the synthesis of 4-chloro-N-(2-pyridin-2-yl-2H-pyrazol-3-yl)-benzenesulfonamide (example 1) the title compound was prepared from 1-(4-methylpyridin-2-yl)-1H-pyrazol-5-amine (commercially available) and 4-chlorobenzene-1-sulfonyl chloride (commercially available). MS(m/e): 349.5 (MH$^+$).

Example 18

4-Ethyl-N-[2-(4-methyl-pyridin-2-yl)-2H-pyrazol-3-yl]-benzenesulfonamide

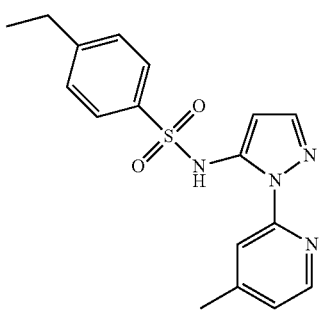 [SMILES: CCc1ccc(S(=O)(=O)Nc2ccnn2-c2cc(C)ccn2)cc1]

In analogy to the procedure described for the synthesis of 4-chloro-N-(2-pyridin-2-yl-2H-pyrazol-3-yl)-benzenesulfonamide (example 1) the title compound was prepared from 1-(4-methylpyridin-2-yl)-1H-pyrazol-5-amine (commercially available) and 4-ethylbenzene-1-sulfonyl chloride (commercially available). MS(m/e): 343.6 (MH$^+$).

Example 19

4-Cyano-N-[2-(4-methyl-pyridin-2-yl)-2H-pyrazol-3-yl]-benzenesulfonamide

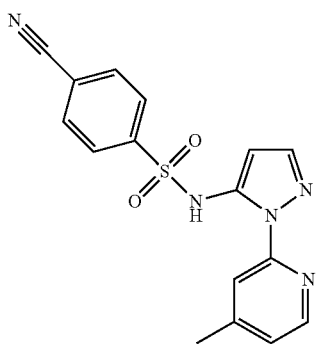 [SMILES: Cc1ccnc(-n2nccc2NS(=O)(=O)c2ccc(C#N)cc2)c1]

In analogy to the procedure described for the synthesis of 4-chloro-N-(2-pyridin-2-yl-2H-pyrazol-3-yl)-benzenesulfonamide (example 1) the title compound was prepared from 1-(4-methylpyridin-2-yl)-1H-pyrazol-5-amine (commercially available) and 4-cyanobenzene-1-sulfonyl chloride (commercially available). MS(m/e): 340.5 (MH$^+$).

Example 20

N-(2-Pyridin-2-yl-2H-pyrazol-3-yl)-4-trifluoromethylsulfanyl-benzenesulfonamide

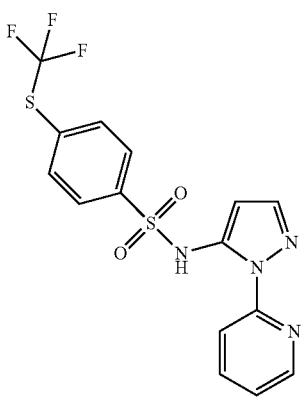 [SMILES: O=S(=O)(Nc1ccnn1-c1ccccn1)c1ccc(SC(F)(F)F)cc1]

In analogy to the procedure described for the synthesis of 4-chloro-N-(2-pyridin-2-yl-2H-pyrazol-3-yl)-benzenesulfonamide (example 1) the title compound was prepared from 2-pyridin-2-yl-2H-pyrazol-3-ylamine (commercially available) and 4-(trifluoromethylthio)benzene-1-sulfonyl chloride (commercially available) and isolated as off-white solid. MS(m/e): 401.5 (MH$^+$).

Example 21

4-Trifluoromethyl-N-[2-(2-trifluoromethyl-pyrimidin-4-yl)-2H-pyrazol-3-yl]-benzenesulfonamide

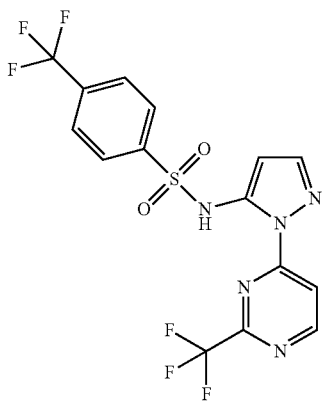 [SMILES: O=S(=O)(Nc1ccnn1-c1ccnc(C(F)(F)F)n1)c1ccc(C(F)(F)F)cc1]

a) 2-(2-Trifluoromethyl-pyrimidin-4-yl)-2H-pyrazol-3-ylamine

A mixture of 4-hydrazinyl-2-(trifluoromethyl)pyrimidine (533 mg, 2.99 mmol) and (E)-3-(dimethylamino)acrylonitrile (288 mg, 2.99 mmol) were heated to 145° C. for 90 min. The mixture was cooled to room temperature, dissolved in DCM (5 mL) and absorbed on isolute HM-N. The mixture was concentrated in vacuo and purified by silica gel chromatography eluting with a gradient formed from heptane and ethyl acetate to yield after evaporation of the product containing fractions 500 mg (73%) of the title compound as yellow solid. MS(m/e): 230.2 (MH$^+$).

b) 4-Trifluoromethyl-N-[2-(2-trifluoromethyl-pyrimidin-4-yl)-2H-pyrazol-3-yl]-benzenesulfonamide In analogy to the procedure described for the synthesis of 4-chloro-N-(2-pyridin-2-yl-2H-pyrazol-3-yl)-benzenesulfonamide (example 1) the title compound was prepared from 1-(2-(trifluoromethyl)pyrimidin-4-yl)-1H-pyrazol-5-amine and 4-(trifluoromethyl)benzene-1-sulfonyl chloride (commercially available). MS(m/e): 436.6 (MH$^+$).

Example 22

2-Fluoro-N-(2-pyridin-2-yl-2H-pyrazol-3-yl)-4-trifluoromethyl-benzenesulfonamide

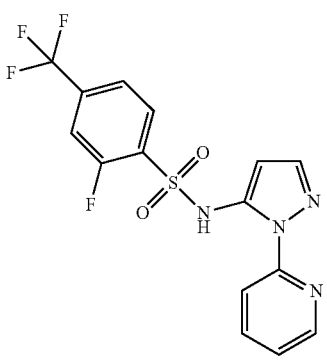 [SMILES: O=S(=O)(Nc1ccnn1-c1ccccn1)c1ccc(C(F)(F)F)cc1F]

2-Fluoro-4-trifluoromethyl-benzenesulfonyl chloride was synthesized in analogy to the flow procedure described in "Preparation of arylsulfonyl chlorides by chlorosulfonylation of in situ generated diazonium salts using a continuous flow reactor" by Malet-Sanz L., Madrzak J., Ley S. V., Baxendale I. R. in Org Biomol Chem 2010, 8, 5324-5332 from 2-fluoro-4-(trifluoromethyl)aniline (commercially available) and subsequently reacted in analogy to the procedure described for the synthesis of 4-chloro-N-(2-pyridin-2-yl-2H-pyrazol-3-yl)-benzenesulfonamide (example 1) with 1-(pyridin-2-yl)-1H-pyrazol-5-amine (commercially available) and isolated as brown solid. MS(m/e): 387.4 (MH$^+$).

Example 23

N-(2-Pyridin-2-yl-2H-pyrazol-3-yl)-4-trifluoromethanesulfonyl-benzenesulfonamide

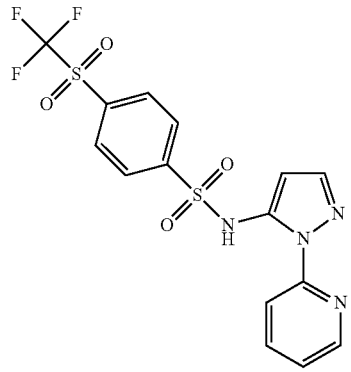 [SMILES: O=S(=O)(Nc1ccnn1-c1ccccn1)c1ccc(S(=O)(=O)C(F)(F)F)cc1]

4-Trifluoromethanesulfonyl-benzenesulfonyl chloride was synthesized in analogy to the flow procedure described in "Preparation of arylsulfonyl chlorides by chlorosulfonylation of in situ generated diazonium salts using a continuous flow reactor" by Malet-Sanz L., Madrzak J., Ley S. V., Baxendale I. R. in Org Biomol Chem 2010, 8, 5324-5332 from 4-(trifluoromethylsulfonyl)aniline (commercially available) and subsequently reacted in analogy to the procedure described for the synthesis of 4-chloro-N-(2-pyridin-2-yl-2H-pyrazol-3-yl)-benzenesulfonamide (example 1) with 1-(pyridin-2-yl)-1H-pyrazol-5-amine (commercially available) and isolated as light brown solid. MS(m/e): 433.5 (MH$^+$).

Example 24

3-Fluoro-N-(2-pyridin-2-yl-2H-pyrazol-3-yl)-4-trifluoromethyl-benzenesulfonamide

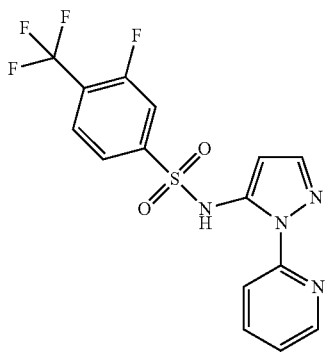 [SMILES: O=S(=O)(Nc1ccnn1-c1ccccn1)c1ccc(C(F)(F)F)c(F)c1]

3-Fluoro-4-trifluoromethyl-benzenesulfonyl chloride was synthesized in analogy to the flow procedure described in "Preparation of arylsulfonyl chlorides by chlorosulfonylation of in situ generated diazonium salts using a continuous flow reactor" by Malet-Sanz L., Madrzak J., Ley S. V., Baxendale I. R. in Org Biomol Chem 2010, 8, 5324-5332 from 3-fluoro-4-(trifluoromethyl)aniline (commercially available) and subsequently reacted in analogy to the procedure described for the synthesis of 4-chloro-N-(2-pyridin-2-yl-2H-pyrazol-3-yl)-benzenesulfonamide (example 1) with 1-(pyridin-2-yl)-1H-pyrazol-5-amine (commercially available) and isolated as light brown solid. MS(m/e): 387.5 (MH$^+$).

Example 25

N-[2-(3-Cyclopropyl-[1,2,4]thiadiazol-5-yl)-2H-pyrazol-3-yl]-4-ethyl-benzenesulfonamide

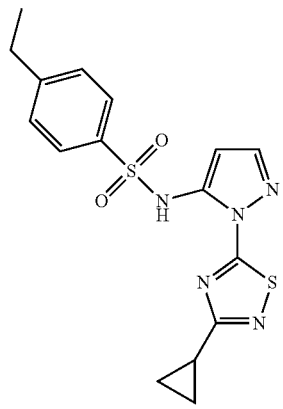 [SMILES: CCc1ccc(S(=O)(=O)Nc2ccnn2-c2nc(C3CC3)ns2)cc1]

a) 2-(3-Cyclopropyl-[1,2,4]thiadiazol-5-yl)-2H-pyrazol-3-ylamine

A mixture of 5-chloro-3-cyclopropyl-1,2,4-thiadiazole (1.22 g, 7.6 mmol) and hydrazine monohydrate (1.9 g, 1.85 ml, 38.0 mmol) in ethanol (50 mL) was heated for 1 h at reflux temperature. The mixture was cooled to room temperature, concentrated in vacuo and dried in high vacuo at 60° C. The residue was combined with 3-(dimethylamino)acrylonitrile (1.83 g, 1.92 ml, 19.0 mmol) and N,N-dimethylacetamide (30 mL) and heated for 2 h to 145° C. After 1 h a further portion of 3-(dimethylamino)acrylonitrile (1.1 g, 1.15 ml, 11.4 mmol) was added. The solution was cooled to room temperature and concentrated in high vacuo. The residue was dissolved in DCM (15 mL), absorbed on Isolute HM, concentrated in vacuo and purified by silica gel chromatography eluting with a gradient formed from heptane and ethyl acetate to yield after evaporation of the product containing fractions 940 mg (60%) of the title compounds as off-white solid. MS(m/e): 208.2 (MH$^+$).

b) N-[2-(3-Cyclopropyl-[1,2,4]thiadiazol-5-yl)-2H-pyrazol-3-yl]-4-ethyl-benzenesulfonamide In analogy to the procedure described for the synthesis of 4-chloro-N-(2-pyridin-2-yl-2H-pyrazol-3-yl)-benzenesulfonamide (example 1) the title compound was prepared from 2-(3-cyclopropyl-[1,2,4]thiadiazol-5-yl)-2H-pyrazol-3-ylamine and 4-ethylbenzene-1-sulfonyl chloride (commercially available). MS(m/e): 374.5 (MH$^+$).

Example 26

4-Chloro-2-fluoro-N-[2-(4-methyl-thiazol-2-yl)-2H-pyrazol-3-yl]-benzenesulfonamide

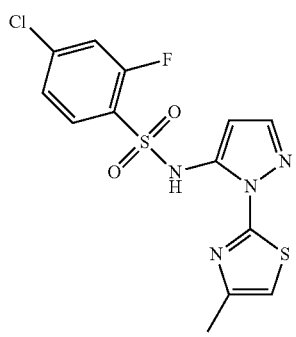 [SMILES: Cc1csc(-n2nccc2NS(=O)(=O)c2ccc(Cl)cc2F)n1]

In analogy to the procedure described for the synthesis of 4-chloro-N-(2-pyridin-2-yl-2H-pyrazol-3-yl)-benzenesulfonamide (example 1) the title compound was prepared from 2-(4-Methyl-thiazol-2-yl)-2H-pyrazol-3-ylamine and 4-chloro-2-fluorobenzene-1-sulfonyl chloride (commercially available) and isolated as off white solid. MS(m/e): 373.5 (MH+).

The compounds of formula I and their pharmaceutically usable addition salts possess valuable pharmacological properties. Specifically, it has been found that the compounds of the present invention have a good affinity to the oxytocin receptor. The compounds were investigated in accordance with the test given hereinafter.

Material and Methods

Cell Culture and Stable Clone Production

Chinese Hamster Ovary (CHO) cells were transfected with expression plasmids encoding either the human V1a, the human Oxytocin (OTR) or the humanV2 receptor, the latter in combination with the chimeric Gqs5 G protein to redirect the signal to Calcium flux. Stable cells were cloned by limiting dilution to yield monoclonal cell lines expressing either human V1a, human V2+Gqs5 or human OTR receptors and selected based on functional responses detected on a fluorometric imaging plate reader (FLIPR) detecting Calcium flux in the cell after receptor activation. The stable cell lines were grown in F-12 K Nutrient Mixture (Kaighns Modification), containing 10% foetal bovine serum (FBS), 1% penicillin-streptomycin, 1% L-glutamate, 200 ug/ml Geneticin at 37° C. in a 10% $CO_2$ incubator at 95% humidity.

Calcium Flux Assays Using Fluorescent Imaging (Fluorometric Imaging Plate Reader, FLIPR)

On the afternoon before the assay, cells were plated at a density of 50,000 cells/well into black 96 well plates with clear bottoms to allow cell inspection and fluorescence measurements from the bottom of each well. The density of cells was sufficient to yield a confluent monolayer the next day. Hanks balanced salt solution, without phenol red, containing 20 mM HEPES (pH 7.3) and 2.5 mM probenecid (assay buffer) was prepared fresh for each experiment. Compound dilutions were made using a Beckman Biomek 2000 laboratory automation workstation, in assay buffer containing 1% DMSO. The dye-loading buffer consisted of a final concentration of 2 µM Fluo-4-AM (dissolved in DMSO and pluronic acid) in assay buffer. The existing culture media was removed from the wells and 100 µl of the dye-loading buffer was added to each well and incubated for approximately 60 min at 37° C. in a 5% $CO_2$ incubator at 95% humidity. Once dye-loaded, the cells were washed thoroughly on an Embla cell washer with the assay buffer to remove any unincorporated dye. Exactly 100 µl assay buffer was left in each well.

Each 96 well plate containing dye-loaded cells was placed into the FLIPR machine and the laser intensity set to a suitable level to detect low basal fluorescence. To test compounds as agonists, 25 µl diluted compound was added to the plate 10 seconds into the fluorescent measurements and fluorescent response was recorded for 5 minutes. The fluorescence data was normalized to the endogenous full agonist dose-response set at 100% for the maximum response and 0% for the minimum. Each agonist concentration-response curve was constructed using a four parameter logistic equation with Microsoft Excel XLFit as follows: Y=Minimum+((Maximum−Minimum)/(1+10$^{(LogEC50-X)nH}$)), where y is the % normalized fluorescence, minimum is the minimum y, maximum is the maximum y, log $EC_{50}$ is the $log_{10}$ concentration which produces 50% of the maximum induced fluorescence, x is the $log_{10}$ of the concentration of the agonist compound and H is the slope of the curve (the Hill Coefficient). The maximum value gives the efficacy of the agonist test compound in percentage. The concentration of agonist that produced a half-maximal response is represented by the $EC_{50}$ value, the logarithm of which yielded the $pEC_{50}$ value.

The following $hEC_{50}$ (uM) for the specific compounds may be provided in table 1:

TABLE 1

| Example | $hEC_{50}$ (uM) |
|---|---|
| 1 | 0.019 |
| 2 | 0.008 |
| 3 | 0.016 |
| 4 | 0.034 |
| 5 | 0.091 |
| 6 | 0.107 |
| 7 | 2.46 |
| 8 | 0.081 |
| 9 | 0.52 |
| 10 | 0.163 |
| 11 | 0.113 |
| 12 | 1.8 |
| 13 | 0.017 |
| 14 | 0.019 |
| 15 | 0.084 |
| 16 | 0.017 |
| 17 | 0.016 |
| 18 | 0.02 |
| 19 | 0.063 |
| 20 | 0.047 |
| 21 | 1.57 |
| 22 | 0.333 |
| 23 | 0.753 |
| 24 | 0.799 |
| 25 | 1.57 |
| 26 | 0.15 |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

| Item | Ingredients | mg/tablet | | | |
|---|---|---|---|---|---|
| | | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| Item | Ingredients | mg/capsule | | | |
|---|---|---|---|---|---|
| | | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The invention claimed is:

1. A method of treating a condition selected from the group consisting of autism, stress, post traumatic stress disorder, anxiety disorders, depression, schizophrenia, psychiatric disorders, memory loss, alcohol withdrawal, drug addiction and Prader-Willi Syndrome, comprising administering a compound of formula I

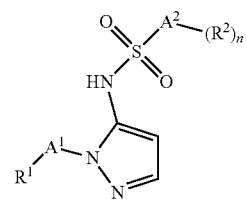

wherein
$A^1$ is phenyl or a five or six membered heteroaryl group, containing 1, 2 or 3 heteroatoms, selected from N or S;
$R^1$ is hydrogen, lower alkyl, halogen, lower alkyl substituted by halogen or cycloalkyl;
$A^2$ is phenyl;
$R^2$ is halogen, lower alkyl, lower alkyl substituted by halogen, lower alkoxy substituted by halogen, cyano, S-lower alkyl substituted by halogen, $S(O)_2$-lower alkyl substituted by halogen;
n is 1 or 2;
or a pharmaceutically acceptable acid addition salt, a racemic mixture or its corresponding enantiomer and/or optical isomers thereof, to a patient in need thereof.

2. A method of treating a condition selected from the group consisting of autism, stress, post traumatic stress disorder, anxiety disorders, depression, schizophrenia, psychiatric disorders, memory loss, alcohol withdrawal, drug addiction and Prader-Willi Syndrome, comprising administering a compound selected from the group consisting of
4-Chloro-N-(2-pyridin-2-yl-2H-pyrazol-3-yl)-benzenesulfonamide
N-(2-Pyridin-2-yl-2H-pyrazol-3-yl)-4-trifluoromethyl-benzenesulfonamide
4-Ethyl-N-(2-pyridin-2-yl-2H-pyrazol-3-yl)-benzenesulfonamide
4-Propyl-N-(2-pyridin-2-yl-2H-pyrazol-3-yl)-benzenesulfonamide
2-Chloro-N-(2-pyridin-2-yl-2H-pyrazol-3-yl)-4-trifluoromethyl-benzenesulfonamide 4-Difluoromethoxy-N-(2-pyridin-2-yl-2H-pyrazol-3-yl)-benzenesulfonamide
4-Chloro-N-[2-(4-fluoro-phenyl)-2H-pyrazol-3-yl]-benzenesulfonamide
4-Cyano-N-(2-pyridin-2-yl-2H-pyrazol-3-yl)-benzenesulfonamide
N-[2-(4-Methyl-thiazol-2-yl)-2H-pyrazol-3-yl]-4-trifluoromethyl-benzenesulfonamide
4-Chloro-N-[2-(4-methyl-thiazol-2-yl)-2H-pyrazol-3-yl]-benzenesulfonamide
4-Ethyl-N-[2-(4-methyl-thiazol-2-yl)-2H-pyrazol-3-yl]-benzenesulfonamide
N-(2-Pyrimidin-2-yl-2H-pyrazol-3-yl)-4-trifluoromethyl-benzenesulfonamide
2,4-Dichloro-N-(2-pyridin-2-yl-2H-pyrazol-3-yl)-benzenesulfonamide
4-Chloro-2-fluoro-N-(2-pyridin-2-yl-2H-pyrazol-3-yl)-benzenesulfonamide
4-(1-Fluoro-ethyl)-N-(2-pyridin-2-yl-2H-pyrazol-3-yl)-benzenesulfonamide
N-[2-(4-Methyl-pyridin-2-yl)-2H-pyrazol-3-yl]-4-trifluoromethyl-benzenesulfonamide
4-Chloro-N-[2-(4-methyl-pyridin-2-yl)-2H-pyrazol-3-yl]-benzenesulfonamide
4-Ethyl-N-[2-(4-methyl-pyridin-2-yl)-2H-pyrazol-3-yl]-benzenesulfonamide
4-Cyano-N-[2-(4-methyl-pyridin-2-yl)-2H-pyrazol-3-yl]-benzenesulfonamide
N-(2-Pyridin-2-yl-2H-pyrazol-3-yl)-4-trifluoromethyl-sulfanyl-benzenesulfonamide
4-Trifluoromethyl-N-[2-(2-trifluoromethyl-pyrimidin-4-yl)-2H-pyrazol-3-yl]-benzenesulfonamide
2-Fluoro-N-(2-pyridin-2-yl-2H-pyrazol-3-yl)-4-trifluoromethyl-benzenesulfonamide
N-(2-Pyridin-2-yl-2H-pyrazol-3-yl)-4-trifluoromethanesulfonyl-benzenesulfonamide
3-Fluoro-N-(2-pyridin-2-yl-2H-pyrazol-3-yl)-4-trifluoromethyl-benzenesulfonamide
N-[2-(3-Cyclopropyl-[1,2,4]thiadiazol-5-yl)-2H-pyrazol-3-yl]-4-ethyl-benzenesulfonamide and
4-Chloro-2-fluoro-N-[2-(4-methyl-thiazol-2-yl)-2H-pyrazol-3-yl]-benzenesulfonamide to a patient in need thereof.

3. A pharmaceutical composition comprising a compound selected from the group consisting of
4-Chloro-N-(2-pyridin-2-yl-2H-pyrazol-3-yl)-benzenesulfonamide
N-(2-Pyridin-2-yl-2H-pyrazol-3-yl)-4-trifluoromethyl-benzenesulfonamide
4-Ethyl-N-(2-pyridin-2-yl-2H-pyrazol-3-yl)-benzenesulfonamide
4-Propyl-N-(2-pyridin-2-yl-2H-pyrazol-3-yl)-benzenesulfonamide
2-Chloro-N-(2-pyridin-2-yl-2H-pyrazol-3-yl)-4-trifluoromethyl-benzenesulfonamide
4-Difluoromethoxy-N-(2-pyridin-2-yl-2H-pyrazol-3-yl)-benzenesulfonamide
4-Chloro-N-[2-(4-fluoro-phenyl)-2H-pyrazol-3-yl]-benzenesulfonamide
4-Cyano-N-(2-pyridin-2-yl-2H-pyrazol-3-yl)-benzenesulfonamide
N-[2-(4-Methyl-thiazol-2-yl)-2H-pyrazol-3-yl]-4-trifluoromethyl-benzenesulfonamide
4-Chloro-N-[2-(4-methyl-thiazol-2-yl)-2H-pyrazol-3-yl]-benzenesulfonamide
4-Ethyl-N-[2-(4-methyl-thiazol-2-yl)-2H-pyrazol-3-yl]-benzenesulfonamide
N-(2-Pyrimidin-2-yl-2H-pyrazol-3-yl)-4-trifluoromethyl-benzenesulfonamide
2,4-Dichloro-N-(2-pyridin-2-yl-2H-pyrazol-3-yl)-benzenesulfonamide
4-Chloro-2-fluoro-N-(2-pyridin-2-yl-2H-pyrazol-3-yl)-benzenesulfonamide
4-(1-Fluoro-ethyl)-N-(2-pyridin-2-yl-2H-pyrazol-3-yl)-benzenesulfonamide
N-[2-(4-Methyl-pyridin-2-yl)-2H-pyrazol-3-yl]-4-trifluoromethyl-benzenesulfonamide
4-Chloro-N-[2-(4-methyl-pyridin-2-yl)-2H-pyrazol-3-yl]-benzenesulfonamide
4-Ethyl-N-[2-(4-methyl-pyridin-2-yl)-2H-pyrazol-3-yl]-benzenesulfonamide
4-Cyano-N-[2-(4-methyl-pyridin-2-yl)-2H-pyrazol-3-yl]-benzenesulfonamide
N-(2-Pyridin-2-yl-2H-pyrazol-3-yl)-4-trifluoromethyl-sulfanyl-benzenesulfonamide
4-Trifluoromethyl-N-[2-(2-trifluoromethyl-pyrimidin-4-yl)-2H-pyrazol-3-yl]-benzenesulfonamide
2-Fluoro-N-(2-pyridin-2-yl-2H-pyrazol-3-yl)-4-trifluoromethyl-benzenesulfonamide
N-(2-Pyridin-2-yl-2H-pyrazol-3-yl)-4-trifluoromethanesulfonyl-benzenesulfonamide
3-Fluoro-N-(2-pyridin-2-yl-2H-pyrazol-3-yl)-4-trifluoromethyl-benzenesulfonamide
N-[2-(3-Cyclopropyl-[1,2,4]thiadiazol-5-yl)-2H-pyrazol-3-yl]-4-ethyl-benzenesulfonamide and
4-Chloro-2-fluoro-N-[2-(4-methyl-thiazol-2-yl)-2H-pyrazol-3-yl]-benzenesulfonamide, or a pharmaceutically acceptable acid addition salt, a racemic mixture or its corresponding enantiomer and/or optical isomers thereof, and a therapeutically inert carrier.

4. A compound selected from the group consisting of
4-Chloro-N-(2-pyridin-2-yl-2H-pyrazol-3-yl)-benzenesulfonamide
N-(2-Pyridin-2-yl-2H-pyrazol-3-yl)-4-trifluoromethyl-benzenesulfonamide
4-Ethyl-N-(2-pyridin-2-yl-2H-pyrazol-3-yl)-benzenesulfonamide
4-Propyl-N-(2-pyridin-2-yl-2H-pyrazol-3-yl)-benzenesulfonamide
2-Chloro-N-(2-pyridin-2-yl-2H-pyrazol-3-yl)-4-trifluoromethyl-benzenesulfonamide
4-Difluoromethoxy-N-(2-pyridin-2-yl-2H-pyrazol-3-yl)-benzenesulfonamide
4-Chloro-N-[2-(4-fluoro-phenyl)-2H-pyrazol-3-yl]-benzenesulfonamide
4-Cyano-N-(2-pyridin-2-yl-2H-pyrazol-3-yl)-benzenesulfonamide
N-[2-(4-Methyl-thiazol-2-yl)-2H-pyrazol-3-yl]-4-trifluoromethyl-benzenesulfonamide
4-Chloro-N-[2-(4-methyl-thiazol-2-yl)-2H-pyrazol-3-yl]-benzenesulfonamide
4-Ethyl-N-[2-(4-methyl-thiazol-2-yl)-2H-pyrazol-3-yl]-benzenesulfonamide
N-(2-Pyrimidin-2-yl-2H-pyrazol-3-yl)-4-trifluoromethyl-benzenesulfonamide
2,4-Dichloro-N-(2-pyridin-2-yl-2H-pyrazol-3-yl)-benzenesulfonamide
4-Chloro-2-fluoro-N-(2-pyridin-2-yl-2H-pyrazol-3-yl)-benzenesulfonamide
4-(1-Fluoro-ethyl)-N-(2-pyridin-2-yl-2H-pyrazol-3-yl)-benzenesulfonamide
N-[2-(4-Methyl-pyridin-2-yl)-2H-pyrazol-3-yl]-4-trifluoromethyl-benzenesulfonamide 4-Chloro-N-[2-(4-methyl-pyridin-2-yl)-2H-pyrazol-3-yl]-benzenesulfonamide
4-Ethyl-N-[2-(4-methyl-pyridin-2-yl)-2H-pyrazol-3-yl]-benzenesulfonamide
4-Cyano-N-[2-(4-methyl-pyridin-2-yl)-2H-pyrazol-3-yl]-benzenesulfonamide
N-(2-Pyridin-2-yl-2H-pyrazol-3-yl)-4-trifluoromethyl-sulfanyl-benzenesulfonamide
4-Trifluoromethyl-N-[2-(2-trifluoromethyl-pyrimidin-4-yl)-2H-pyrazol-3-yl]-benzenesulfonamide
2-Fluoro-N-(2-pyridin-2-yl-2H-pyrazol-3-yl)-4-trifluoromethyl-benzenesulfonamide
N-(2-Pyridin-2-yl-2H-pyrazol-3-yl)-4-trifluoromethanesulfonyl-benzenesulfonamide
3-Fluoro-N-(2-pyridin-2-yl-2H-pyrazol-3-yl)-4-trifluoromethyl-benzenesulfonamide
N-[2-(3-Cyclopropyl-[1,2,4]thiadiazol-5-yl)-2H-pyrazol-3-yl]-4-ethyl-benzenesulfonamide and
4-Chloro-2-fluoro-N-[2-(4-methyl-thiazol-2-yl)-2H-pyrazol-3-yl]-benzenesulfonamide or a pharmaceutically acceptable acid addition salt, a racemic mixture or its corresponding enantiomer and/or optical isomers thereof.

5. A compound of formula IA,

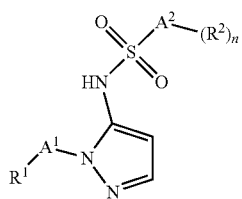

wherein
$A^1$ is thiazolyl, pyrimidinyl or 1,2,4-thiadiazolyl;
$R^1$ is hydrogen, lower alkyl, halogen, lower alkyl substituted by halogen or cycloalkyl;
$A^2$ is phenyl;
$R^2$ is halogen, lower alkyl, lower alkyl substituted by halogen, lower alkoxy substituted by halogen, cyano, S-lower alkyl substituted by halogen, $S(O)_2$-lower alkyl substituted by halogen;
n is 1 or 2;
or a pharmaceutically acceptable acid addition salt, a racemic mixture or its corresponding enantiomer and/or optical isomers thereof.

6. A compound selected from the group consisting of
N-[2-(4-Methyl-thiazol-2-yl)-2H-pyrazol-3-yl]-4-trifluoromethyl-benzenesulfonamide
4-Chloro-N-[2-(4-methyl-thiazol-2-yl)-2H-pyrazol-3-yl]-benzenesulfonamide
4-Ethyl-N-[2-(4-methyl-thiazol-2-yl)-2H-pyrazol-3-yl]-benzenesulfonamide
N-(2-Pyrimidin-2-yl-2H-pyrazol-3-yl)-4-trifluoromethyl-benzenesulfonamide
4-Trifluoromethyl-N-[2-(2-trifluoromethyl-pyrimidin-4-yl)-2H-pyrazol-3-yl]-benzenesulfonamide
N-[2-(3-Cyclopropyl-[1,2,4]thiadiazol-5-yl)-2H-pyrazol-3-yl]-4-ethyl-benzenesulfonamide and
4-Chloro-2-fluoro-N-[2-(4-methyl-thiazol-2-yl)-2H-pyrazol-3-yl]-benzenesulfonamide.

7. A process for preparation of a compound of formula IA, or a pharmaceutically acceptable acid addition salt, a racemic mixture or its corresponding enantiomer and/or optical isomers thereof, which process comprises
a) reacting a compound of formula

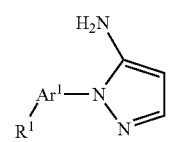

with a compound of formula

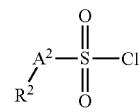

to afford the compound of formula IA
wherein formula IA is as follows

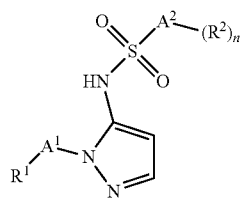

wherein
$A^1$ is thiazolyl, pyrimidinyl or 1,2,4-thiadiazolyl;
$R^1$ is hydrogen, lower alkyl, halogen, lower alkyl substituted by halogen or cycloalkyl;
$A^2$ is phenyl;
$R^2$ is halogen, lower alkyl, lower alkyl substituted by halogen, lower alkoxy substituted by halogen, cyano, S-lower alkyl substituted by halogen, $S(O)_2$-lower alkyl substituted by halogen;
n is 1 or 2.

* * * * *